United States Patent [19]
Wakamatsu et al.

[11] Patent Number: 4,810,818
[45] Date of Patent: Mar. 7, 1989

[54] PROCESS FOR PRODUCING ALPHA-ASPARTYL-L-PHENYLALANINE METHYL ESTER HAVING AN IMPROVED SOLUBILITY

[75] Inventors: Hidetoshi Wakamatsu, Shin-nanyo; Shigeaki Irino, Yamaguchi; Tsuneo Harada; Akira Tokuda, both of Shin-nanyo; Kiyotaka Oyama, Hikari, all of Japan

[73] Assignee: Toyo Soda Manufacturing Co., Ltd, Yamaguchi, Japan

[21] Appl. No.: 78,707

[22] Filed: Jul. 28, 1987

[30] Foreign Application Priority Data

Jul. 28, 1986 [JP] Japan ............................ 61-175568

[51] Int. Cl.$^4$ ........................................... C07C 101/02
[52] U.S. Cl. ..................................................... 560/41
[58] Field of Search ........................ 560/41; 530/801; 426/548; 34/10, 26, 31

[56] References Cited

U.S. PATENT DOCUMENTS 4,579,747  4/1986  Sugiyama et al. .................. 426/548

FOREIGN PATENT DOCUMENTS 57-42623  9/1982  Japan .
59-95862  6/1984  Japan .
59-172444  9/1984  Japan .
60-37949  2/1985  Japan .

OTHER PUBLICATIONS

Perry et al, *Chemical Engineers' Handbook*, 5th ed, McGraw-Hill, New York, pp. 20-4 to 20-16 (1973).
"Application Potential for Aspartame in Low Calorie and Dietetic Foods", In Low Calorie and Special Dietary Foods, pp. 59-114, CRC Press 1978 CFR 21, Food and Drugs revised as of Apr. 1, 1981.

*Primary Examiner*—Bruce D. Gray
*Attorney, Agent, or Firm*—Nixon & Vanderhye

[57] ABSTRACT

A process for producing dry α-L-aspartyl-L-phenylalanine methyl ester having an improved solubility from wet crystals of α-L-aspartyl-L-phenylalanine methyl ester having a water content of at least 20% by weight, which comprises drying the wet crystals at a temperature of higher than 50° C. to obtain moist crystals having a water content of less than 20 and more than 15% by weight, then drying the moist crystals at a temperature of not higher than 50° C. to obtain semi-dry crystals having a water content of less than 5% by weight, and further drying the semi-dry crystals at a temperature of higher than 50° C. to obtain dry crystals of α-L-aspartyl-L-phenylalanine methyl ester.

5 Claims, No Drawings

PROCESS FOR PRODUCING ALPHA-ASPARTYL-L-PHENYLALANINE METHYL ESTER HAVING AN IMPROVED SOLUBILITY

The present invention relates to a process for producing α-L-aspartyl-L-phenylalanine methyl ester (hereinafter referred to as Aspartame) having an improved solubility.

Heretofore, various methods have been proposed to obtain Aspartame having an excellent solubility. For example, it has been proposed to granulate Aspartame together with an excipient having an excellent solubility, to form it into disintegrating tablets in combination with an excipient and a disintegrator, or to form it into effervescing tablets in combination with an effervescing agent and a neutralizing agent. Another method is known wherein a specific amount of water is added to Aspartame II type crystals, followed by mixing, granulating and drying (Japanese Unexamined Patent Publication No. 95862/1984). It is known that there are two types of Aspartame crystals, i.e. I and II type crystals (Japanese Unexamined Patent Publication Nos. 172444/1984 and 37949/1985). Aspartame II type crystals have a low hygroscopicity and an excellent storage stability, as compared with the I type crystals. Therefore, the process for producing Aspartame II type crystals have been extensively studied. However, no substantial studies have been made on Aspartame I type crystals.

Aspartame has poor dispersibility and solubility in water. In its application to food, Aspartame is likely to form agglomerates due to the poor dispersibility and solubility when dissolved, which make the operation of dissolving it in water difficult and time-consuming.

In conventional methods, it is necessary to dissolve Aspartame in water or to form it into a slurry once. Therefore, there are problems with respect to the operations, the process control and costs for energy. On the other hand, if other substances are mixed to Aspartame to improve the solubility, the presence of such substances may likely be a problem depending upon a particular use. Therefore, there is strong demand for highly pure Aspartame having an excellent solubility.

According to the studies by the present inventors, of the above-mentioned two types of Aspartame crystals, the I type crystals are far superior in the solubility to the II type crystals. A product obtained by drying wet Aspartame crystals by an industrial method, is usually a mixture of the I and II type crystals. Therefore, it is also an important technical subject to develop an industrial process for the production of the I type crystals containing no or only a small amount of the II type crystals.

The present invention provides a process for producing dry α-L-aspartyl-L-phenylalanine methyl ester having an improved solubility from wet crystals of α-L-aspartyl-L-phenylalanine methyl ester having a water content of at least 20% by weight, which comprises drying the wet crystals at a temperature of higher than 50° C. to obtain moist crystals having a water content of less than 20 and more than 15% by weight, then drying the moist crystals at a temperature of not higher than 50° C. to obtain semi-dry crystals having a water content of less than 5% by weight, and further drying the semi-dry crystals at a temperature of higher than 50° C. to obtain dry crystals of α-L-aspartyl-L-phenylalanine methyl ester.

In the present invention, the wet crystals of Aspartame used as the starting material to obtain dry Aspartame having an improved solubility, may be prepared by any crystallization and separation methods. Thus, there is no restriction as to the method of producing wet Aspartame crystals. Namely, wet Aspartame crystals used in the present invention may be prepared by an appropriate crystallization method, followed by a solid-liquid separation. Wet Aspartame crystals prepared may be or may not be treated by a granulator. For the treatment by a granulator, any type of a granulator such as an extrusion granulation type, a compression granulation type may be employed. In the case where wet Aspartame crystals are treated by an extrusion type granulator, cylindrical granules can be obtained by passing wet Aspartame crystals through a screen having a mesh size of from 0.1 to 10.0 mm, preferably from 0.5 to 5 mm, more preferably from 2.0 to 4.0 mm.

According to the present invention, there is no particular restriction as to conditions for drying wet Aspartame crystals to a water content range of less than 20 and more than 15% by weight based on the weight of wet Aspartame crystals except for that the temperature at which the water content of the crystals is reduced to a value of less than 20% and more than 15%, be maintained higher than 50° C. However, Aspartame is not stable at a high temperature, and when it is dried at a high temperature, a part of Aspartame is readily converted to a diketopiperadine derivative. The diketopiperadine derivative is non-toxic and safe, but it lacks in sweetness, thus leading to a loss of overall sweetness. Therefore, Aspartame is dried preferably at a temperature of not higher than 80° C.

Irrespective of the drying method employed, Aspartame maintains the crystal form having an excellent solubility (the I type crystal form) till the water content is reduced to about 15% by weight. The conversion from the I type to the II type takes place at a water content range of from 5 to 15% by weight. Therefore, it is desirable that Aspartame containing a water content of from 5 to 15% by weight is treated at a temperature as low as possible, preferably at most 50° C.

Any method and device for drying Aspartame may be used in the present invention. A conventional method such as air stream drying in a fixed bed system or drying in a fluidized bed system may be employed.

Once the water content has been reduced to a level of less than 5% by weight, further drying may efficiently be conducted at a temperature of higher than 50° C.

Thus, a dry Aspartame product having an excellent solubility (the I type crystals) can be obtained.

Now, the present invention will be described in further detail with reference to Examples. However, it should be understood that the present invention is by no means restricted to these specific Examples.

In the Examples, the ratio of I type crystals (i.e. the ratio of the I type crystals to the total amount of the I and II type crystals) was determined as follows: Standard samples of the I and II type crystals were mixed at various ratios, and a calibration curve was prepared based on strength ratios of the respective X-ray diffraction specific peaks, where the I and II type crystals exhibit the X-ray diffraction specific peaks at angles ($2\theta$) of diffraction of 4.4° and 5.0°, respectively. Then, the ratio of the I type crystals was determined by comparing the strength ratio of each sample with the calibration curve.

In the Examples, the solubility of Aspartame crystals was determined by measuring the duration till 1 g of Aspartame crystals which was added to 500 ml of distilled water at 20° C., followed by stirring (by a magnetic stirrer at 200 r.p.m.), was completely dissolved as visually observed.

EXAMPLE 1

Wet Aspartame crystals (30 kg, the water content of 60.3% by weight based on the wet crystals) obtained by a solid-liquid separation by means of a centrifugal separator, was extruded through a screen having a mesh size of 2 mm, and granulated, and then dried in a fluidized-bed drier by means of a hot air stream of 70° C. to a water content of 15% by weight. Then, the temperature of the hot air stream was lowered to 50° C., and the drying operation was continued to reduce the water content to 4.9% by weight. Then, the temperature of the hot air stream was raised to 70° C. again, and the drying operation was continued to obtain 12.3 kg of a dry Aspartame product having the water content of 2.6% by weight.

On the other hand, for the purpose of comparison, the same granulated wet crystals (30 kg) were dried in the fluidized drier by means of a hot air stream of 70° C. to a water content of 2.0% by weight (12.2 kg, Comparative Example 1).

TABLE 1

| Number of Example or Comparative Example | Solubility of the product and ratio of I type crystals | |
|---|---|---|
| | Solubility (min) | Ratio of I type crystals (%) |
| Example 1 | 5–6 | 98 |
| Comparative Example 1 | 13–14 | 25 |

EXAMPLES 2 to 5

Granulated wet Aspartame crystals (30 kg) prepared in the same manner as in Example 1, were dried in the fluidized-bed drier by means of a hot air stream of 50° C. to a water content of from 3.2 to 5.0% by weight. Then, the temperature of the hot air stream was raised to 70° C., and the drying operation was continued to obtain a dry Aspartame product (12.2 kg) having a water content of from 1.9 to 2.3% by weight.

The results at various water contents are shown in the following Table.

TABLE 2

| Number of Example or Comparative Example | Water content after drying at 50° C. (%) | Water content after drying at 70° C. (%) | Solubility (min.) | Ratio of I type crystals (%) |
|---|---|---|---|---|
| Example 2 | 5.0 | 2.3 | 5–6 | 90 |
| Example 3 | 4.3 | 2.1 | 5–6 | 100 |
| Example 4 | 3.8 | 2.0 | 4–5 | 98 |
| Example 5 | 3.2 | 1.9 | 4–5 | 100 |
| Comparative Example 2 | 14.5 | 2.0 | 13–14 | 60 |
| Comparative Example 3 | 10.1 | 1.9 | 15–16 | 51 |
| Comparative Example 4 | 8.2 | 2.1 | 14–15 | 64 |
| Comparative Example 5 | 6.0 | 2.3 | 7–8 | 78 |

As is apparent from the foregoing description, according to the present invention, it is possible to obtain dry Aspartame having an excellent solubility without disadvantages with respect to the process control and costs for energy, or without necessity of mixing it with other substances.

The dry Aspartame product having an improved solubility of the present invention is widely useful as a sweetener for soft drinks, a table sweetener or a sweetener for other foods.

We claim:

1. A process for producing dry crystals of α-L-aspartyl-L-phenylalanine methyl ester in which the ratio of type I crystals is at least 90% and having an improved solubility, said dry crystals being produced from wet crystals of α-aspartyl-L-phenylalanine methyl ester having a water content of at least 20% by weight, said process comprising:
   (a) drying the wet crystals at a temperature higher than 50° C. to obtain moist crystals having a water content of less than 20 and more than 15% by weight; then
   (b) drying the moist crystals at a temperature not higher than 50° C. to obtain semi-dry crystals having a water content of less than 5% by weight; and
   (c) further drying the semi-dry crystals at a temperature higher than 50° C. to obtain said dry crystals of α-L-aspartyl-L-phenylalanine methyl ester.

2. The process according to claim 1, wherein the wet crystals are granulated by a granulator before drying.

3. The process according to claim 2, wherein the wet crystals are granulated to form granules having a diameter of from 0.1 to 10.0 mm.

4. The process according to claim 1, wherein the temperature for drying the wet crystals and the temperature for drying the semi-dry crystals are lower than 80° C.

5. The process according to claim 1, wherein each drying step is conducted under atmospheric pressure.

* * * * *